United States Patent [19]
Wolcott

[11] Patent Number: 5,814,550
[45] Date of Patent: Sep. 29, 1998

[54] COLLOIDAL SILICA FILMS FOR CELL CULTURE

[75] Inventor: Christine C. Wolcott, Horseheads, N.Y.

[73] Assignee: Corning Incorporated

[21] Appl. No.: 721,152

[22] Filed: Sep. 26, 1996

Related U.S. Application Data

[60] Provisional application No. 60/005,039 Oct. 6, 1995.
[51] Int. Cl.⁶ ........................................... C12M 3/04
[52] U.S. Cl. ................ 435/402; 435/289.1; 435/305.1
[58] Field of Search ........................... 117/76, 152, 169; 428/403; 435/305.1, 325, 395, 402, 284, 283.1, 289.1

[56] References Cited

U.S. PATENT DOCUMENTS

| | | | |
|---|---|---|---|
| 3,676,189 | 7/1972 | Woodward et al. | 117/76 |
| 3,754,984 | 8/1973 | Payne | 117/152 |
| 4,243,692 | 1/1981 | Scholze et al. | 427/2 |
| 4,448,884 | 5/1984 | Henderson | 435/241 |
| 4,661,407 | 4/1987 | Henderson | 428/403 |

OTHER PUBLICATIONS

Barnes et al. Methods for Growth of Cultured Cells in Serum–Free Medium. Analytical Biochemistry, 1980, vol. 102, pp. 255–270, entire document.

*Primary Examiner*—David Guzo
*Assistant Examiner*—Irem Yucel
*Attorney, Agent, or Firm*—Thomas R. Beall

[57] ABSTRACT

Methods for producing thin colloidal silica films on substrates, such as corona treated polystyrene, are provided. The dried films are characterized as 50 nm thick, high silanol, homogenous, high surface area, porous, uncracked, adherent, wetting, negatively charged, and gamma radiation stable. Several differential advantages of the colloidal silica films were demonstrated in epithelial cell culture, especially regarding primary cultures in serum free media. Cell responses to the films were increased explant adhesion, increased cell growth rate, and increased expression of differentiated function before and after subculture as compared to tissue culture polystyrene.

22 Claims, 5 Drawing Sheets

COLLOIDAL SILICA FILMS FOR CELL CULTURE

This application claims priority to Provisional U.S. Application number 60/005,039, filed Oct. 6, 1995.

BACKGROUND OF THE INVENTION

1. Field of the Invention

This invention relates to cell culture and, in particular, to the provision of surfaces which are conducive to the attachment and growth of cells, including primary cells, in culture.

2. Description of the Prior Art

Up to the 1970's, soda lime silicate glass was the primary material used in tissue culture. A standard culture vessel in this time period was a prescription bottle made by the Brockway Glass Company of Brockway, Pa. These glass vessels became notably improved for tissue culture use after repeated washing, i.e., after surface corrosion. See Rappaport, C., J. P. Poole and H. P. Rappaport, "Studies of the Surfaces Required for Growth of Mammalian Cells in Synthetic Medium", *Exp. Cell Res.*, Vol. 20, 1960, pages 465–510.

In the 1970's, injection molded polystyrene (PS) was introduced as a tissue culture material. Today, in addition to polystyrene, polymers such as polycarbonate (PC) and polyethylene terephthalate (PET) are also commonly used as growth substrates for adhesion dependent mammalian cells in culture. Sheets of these materials or injection molded vessels are examples of the geometries commonly employed.

Most polymers are treated with an electrical plasma discharge to improve cell adhesion by allowing the surface to become hydrophilic. When the polymer is polystyrene, these surfaces are called tissue culture PS or simply TCPS. The increased wettability and surface oxidation (—OH and —COOH groups) of TCPS permits adsorption of cell adhesion molecules from surrounding media, and therefore cell adhesion. Adding substrate porosity has improved polymer surfaces for some applications, especially where expression of differentiated function is required.

Polymer surfaces are acceptable for most cell culture applications, especially those involving established cell lines which are well adapted to attachment and division on tissue culture PS. These PS surfaces, however, are in some cases unsuitable for certain applications, such as, primary cell cultures and serum-free cell cultures.

Most mammalian cell culture is performed using 5–10% fetal bovine serum in growth media to enhance cell attachment and support cell viability and proliferation. Those culturing hard-to-attach cells commonly modify polymer substrates by coating with extracellular matrix (ECM) components either singly or in combination to improve cell adhesion. Examples of ECM components are collagen, fibronectin and laminin. Peptides having sequences derived from ECM components are also used for this purpose. See, for example, Hubbell et al., U.S. Pat. No. 5,278,063. Serum and ECM coatings can be costly, time consuming to evaluate or apply, and nonhomogeneous from lot to lot; therefore surfaces that reduce or eliminate the need for serum or ECM coatings are desired.

Glass-coated microcarriers produced by SoloHill Labs, Inc., of Ann Arbor, Mich., have been used to grow anchorage-dependent cells in culture. SoloHill describes its beads as having a smooth surface. MRC-5 cells grown on the beads are reported to have higher cell viability after trypsinization than cells grown on DEAE-dextran microcarriers. The glass substrate is also reported to cause an increased production of virus centers (viable, virus-infected cells) in culture compared to either dextran or collagen gel. See Variani, J., M. J. Bendelow and W. J. Hillegas, "The Effect of Substrate on the Production of Infectious Virus by Cells in Culture", *J. of Biol. Stand.*, Vol. 16, 1988, pages 333–338.

Cells grown on the SoloHill beads are said to attach via long, slender filopodia, allowing the cells to be readily detached. U.S. Pat. Nos. 4,029,045, 4,448,884, 4,564,532, and 4,661,407 relate to these carriers. As described therein, glass coatings are applied to polymeric beads by chemical vapor deposition techniques (U.S. Pat. Nos. 4,029,045, 4,564,532, and 4,661,407) or rf-sputtering techniques (U.S. Pat. Nos. 4,029,045 and 4,448,884). The use of colloidal silica to produce a tissue culture surface is neither mentioned or suggested.

Microcarriers having the opposite configuration, i.e., glass on the inside and an organic polymer on the outside, have been distributed by QDM Laboratories of Antrim, Northern Ireland, under the trademark, CELLFAST. The particles are described as having indentations in which individual cells can anchor and grow. See PCT Patent Publication No. WO86/07345, which describes production of glass beads by combining a solution of a soluble silicate, a solution of an organic polymer, and an acidic solution, and PCT Patent Publication No. WO87/02703, which describes polymer-coating of beads of the type disclosed in WO86/07345 to produce indentation-containing microcarriers for cell culture.

The use of silicic acid heteropolycondensates as coating compositions in the culture of living cells is described in Scholze et al., U.S. Pat. No. 4,243,692. In accordance with this patent, a substituted silane, a functional silane, and a hydrolyzable silicic acid derivative are simultaneously condensed to produce the heteropolycondensate. In some cases, part of the condensation reaction is carried out on the support which is being coated. The process of this patent does not involve the application of silicon dioxide ($SiO_2$) particles to a substrate.

The use of silica gels produced from colloidal silica as a medium for growing microorganisms, e.g., as a substitute for an agar medium, is discussed in Pramer, D., "The Influence of Physical and Chemical Factors on the Preparation of Silica Gel Media", *Applied Microbiol.*, Vol. 5, pages 392–395, 1957; Kingsbury, J. M. and Barghoorn, E. S, "Silica Gel as a Microbiological Medium: Potentialities and a New Method of Preparation", *Applied Microbiol.*, Vol. 2, pages 5–8, 1954; and Temple, K. L., "A New Method for the Preparation of Silica Gel Plates", *J. Bacteriol.*, Vol. 57, page 57, 1949. Unlike the present invention, the goal of these early uses of colloidal silica was to retain water in the gel (i.e., to minimize syneresis), rather than to remove water during the coating process so as to produce a highly cross-linked, substantially permanent film on the substrate undergoing coating.

SUMMARY OF THE INVENTION

In view of the foregoing, it is an object of the present invention to provide improved surfaces for use in growing cells in tissue culture. In particular, it is an object of the invention to provide surfaces which are conducive to the growth of primary cells.

It is a further object of the invention to provide surfaces which can be readily applied to substrates currently used in tissue culture work or which may be developed in the future, such as, petri dishes, coverslips, flasks, cell cubes, multiwell plates, cell well inserts, and the like.

To achieve the foregoing and other objects, the invention provides apparatus for performing cell culture which comprises a substrate and a film of colloidal silica which is applied to at least a portion of the substrate. The invention also provides methods for producing such apparatus in which an aqueous solution of colloidal silica is applied to the substrate and dried to form the desired film.

As described in detail below, in accordance with the invention it has been found that substrates coated with a colloidal silica film elicit responses from cells in culture which are significantly different from the uncoated substrate. In particular, colloidal silica films provide a growth surface which induces a more in vivo-like cell response, especially for primary cells.

As used herein, the term "colloidal silica film" refers to a film formed on a substrate by applying an aqueous solution of colloidal silica (i.e., a solution containing silica particles whose dimensions and concentration are small enough so that the particles remain substantially dispersed within the solution at a preselected temperature, e.g., a temperature of 25° C.) to a substrate and drying the solution so as to produce a film on the substrate as a result of cross-linking of the silica particles as a result of the removal of water. The silica particles are preferably charged to help prevent cross-linking in the aqueous solution.

The foregoing figures, which are incorporated in and constitute part of the specification, illustrate various aspects of the invention, and together with the description, serve to explain the principles of the invention. It is to be understood, of course, that both the figures and the description are explanatory only and are not restrictive of the invention.

DESCRIPTION OF THE PREFERRED EMBODIMENTS

As discussed above, the present invention relates to the preparation of cell culture surfaces by the application of colloidal silica films to substrates.

A variety of substrates having a variety of geometric configurations and made of a variety of materials can be used in the practice of the invention. Examples include substrates made of organic materials, such as, polystyrene, polycarbonate, and polyethylene terephthalate, and substrates made of inorganic materials, such as, glass, ceramics, glass-ceramics, and metals. In addition, the substrate can be composed of more than one material and can have, for example, a layered configuration. Both solid and porous substrates can be used. Examples of possible configurations for the substrate include petri dishes, coverslips, slides, plates, flasks, cell cubes, multiwell plates, cell well inserts, etc. All or part of the surface of the substrate can be coated with the inventive film of the invention as desired.

The substrate needs to have a wettable surface so that a bond can be achieved between the silica of the colloidal silica coating solution and the substrate. In the case of polymeric materials, such as polystyrene, such a wettable surface can be achieved by, for example, plasma or corona treatment.

The films of the invention are formed by applying an aqueous solution of colloidal silica to the substrate to be coated and then removing water to produce the desired film. The films are characterized by a thickness which is preferably less than about 100 nm and most preferably about 50 nm, a relatively high Si—OH content, and preferably at least some porosity.

The silica particles in the aqueous solution have dimensions small enough so that the particles remain dispersed at, for example, room temperature. A suitable average diameter for these particles is about 12 nm, although particles having larger or smaller average diameters can be used if desired. The distribution of the silica particles about their average value can be used to control the porosity of the finished film. Specifically, by using a combination of small and large particles the porosity can be reduced since the small particles will tend to fill the spaces between the large particles.

The silica particles are preferably pure $SiO_2$, although particles which have been surface modified by the inclusion of, for example, alumina can be used if desired. In particular, the inclusion of alumina produces particles having a positive charge which may be desirable for certain types of cells.

The aqueous solution as applied to the substrate will generally have a relatively low concentration of silica particles, e.g., on the order of about 10 wt. % and preferably below about 5 wt. %, to ensure the formation of a thin film. The remainder of the solution is primarily water with some counter ions, as needed to maintain the silica particles in suspension. The solution is preferably free of organic materials, although film forming polymers can be included, if desired, provided they do not substantially interfere with the film forming process, the number of active silanol sites, or the growth of cells on the finished film. Organics included in the aqueous solution can be removed from the dried film at least to some extent by an oxygen plasma treatment if desired. Also, washing of the dried film, e.g., in an acid solution, can also be used to remove organics if desired.

The aqueous solution of silica particles can be applied to the substrate in various ways, a preferred approach being by spin coating because, among other things, with spin coating, the thickness of the film can be readily controlled by simply varying the rate at which the substrate is spun. The viscosity of the aqueous solution is an additional variable, in combination with spin speed, which can be used to control film thickness. Viscosity increases can be achieved by, for example, adding organics to the aqueous solution.

Other possible coating approaches include atomizing the solution and applying it to the substrate as a mist, dipping the substrate in the solution, and the like. Whatever method is used, the final film must be thin enough to avoid cracking and peeling.

Once applied to the substrate, the coating must be dried to form the desired film. Drying can take place by simple evaporation at room temperature or can be performed at an elevated (or reduced) temperature if desired. Again, the drying must be conducted at a rate such that the film does not develop cracks which can lead to peeling. Also, the drying should be conducted at a temperature which does not lead to the bleeding of materials from the substrate. In addition, the drying should be conducted at a temperature which does not result in a substantial loss of silanol groups from the film, e.g., a temperature below about 120° C. Further, when organic substrates are used, the drying temperature must be low enough so that significant deformation of the substrate does not take place.

Although it is generally preferred to use the colloidal silica films of the present invention as produced, modifications of the films can be performed if desired. For example, the films can be used as a bonding agent for subsequent layers, such as, a collagen layer, an ECM layer, or a layer of dialdehyde starch (see U.S. Pat. No. 5,281,660). Also, organofunctional silanes can be applied to the films in a vapor or liquid phase to add surface chemistry flexibility.

The films can also be modified with bioactive inorganic ions (e.g., Ca, Mg) before tissue culture. (See Cheung, U.S. Pat. No. 4,757,017 for a discussion of the mitogenic effects of calcium surfaces.) When surface modifications are done, the pH of the system needs to be controlled to avoid substantial dissolution of the colloidal silica film.

Localized derivatization can also be performed on the film to obtain specialized forms of tissue cell growth. See, for example, Kleinfeld et al., "Controlled Outgrowth of Dissociated Neurons on Patterned Substrates", *J. of Neurosci*, Vol. 8, No. 11, 1988, pages 4098–4120. Rather than using derivatization, patterned growth can be achieved by producing localized wetting and non-wetting areas on the substrate by, for example, localized plasma or cerona treatment. The silica coating solution will only adhere to the wetting areas thus producing a patterned surface for subsequent cell growth.

Discussions of colloidal silica dispersions and their use in producing coatings can be found in Doban U.S. Pat. No. 2,906,658, Iler, U.S. Pat. Nos. 2,833,661 and 3,773,776, Payne, U.S. Pat. No. 3,754,984, Wolinski, U.S. Pat. No. 2,909,443, and Woodward, U.S. Pat. No. 3,676,189.

As described in detail below, in accordance with certain preferred embodiments of the invention, colloidal silica dispersions were applied by spin coating to corona-treated PS dishes. The spin coating resulted in 50 nm thick adherent films which were crack-free, clear, microporous and which had a surface rich in reactive silanol groups. These films were extremely wetting and slightly soluble in buffer. The films were found to be superior to uncoated corona-treated PS in the culture of primary cells in serum-free media. This is an important advantage of the invention since as is known in the art, primary cells are difficult to culture in serum-free media.

Without intending to limit it in any manner, the present invention will be more fully described by the following examples.

EXAMPLE 1

Coating of Substrates with Colloidal Silica Films

1. Substrates

Conventional corona-treated 35 mm polystyrene petri dishes manufactured by Corning Costar Inc. (Oneonta, N.Y.) were used as the substrates. Some of the dishes were unsterile at the time of coating, while others were gamma irradiated for sterilization before coating.

2. Colloidal Silica Coating Solutions

Twenty to forty milliliter colloidal silica coating solutions were prepared using DuPont's LUDOX brand colloidal silica, grade HS-40 (DuPont Specialty Chemicals, Wilmington, Del.). As reported by the manufacturer, this grade has the following properties: particle charge—negative; average particle diameter—12 nm; specific surface area—220 $m^2/gm$; $SiO_2$ content—40 wt %; stabilizing counter ion—sodium; $SiO_2/Na_2O$ ratio (by wt)—95; pH at 25° C.–9.7. See "Ludox Colloidal Silica—Properties, Uses, Storage, and Handling," DuPont Specialty Chemicals, Wilmington, Del., Publication No. H-47771, January, 1994.

Coating solutions were also prepared using LUDOX grade SK. As reported by the manufacturer, this grade has the following properties: particle charge—negative; average particle diameter—12 nm; specific surface area—230 $m^2/gm$; $SiO_2$ content—25 wt %; pH at 25° C. 4–7. Rather than using a stabilizing counter ion (e.g., sodium), the surfaces of the silica particles used in grade SK are modified with alumina so that they have a permanent negative charge, irrespective of the pH of the solution. In addition, the SK grade includes a water soluble, film forming polymer (polyvinyl alcohol). See "Ludox Colloidal Silica—Properties, Uses, Storage, and Handling," DuPont Specialty Chemicals, Wilmington, Del., Publication No. H-47771, January, 1994.

The coating solutions were prepared just prior to coating of the substrates by diluting the HS-40 dispersion with deionized water to make a 10% (vol/vol) solution (10× dilution). In some experiments, a 50% (vol/vol) solution was used (2× dilution). The coating solutions made with LUDOX SK were used at a 2× dilution.

Although the pH of the HS-40 solution remained >9 after dilution, small amounts of silica whiskers formed within hours after dilution. The use of pH 9 water, as opposed to deionized water, has been found to eliminate whisker formation.

The diluted dispersion was filtered using a $0.2\mu$ non-sterile surfactant-free cellulose acetate syringe filter (Nalgene, Rochester, N.Y., Catalog No. 191-2020). No significant loss of silica occurred during filtration as determined by chemical analysis (DCP) of the filtrate. LUDOX HS-40 is certified as 40 wt % $SiO_2$, and the 10× diluted and filtered solution was found to have a silica concentration of 4.7 wt %.

3. Coating Procedure

The polystyrene petri dishes were spin coated one at a time using a benchtop photo-resist spinner (Headway Research, Inc., Garland, Tex., Catalog No. 1-EC101D-R485) placed inside a laminar flow hood. The spinner consists of a controller connected to a ¾ inch (1.9 cm) vacuum spinning chuck and a foot pedal switch.

In order to ensure that the bottom surface of each dish was completely coated before spinning, an excess of coating solution (0.2–0.4 ml) was dropped onto each dish using a pasture pipette, and the dish swirled by hand. The pasture pipette was washed in 0.1N NaOH after each use to prevent formation of particles of polymerized silica on the pipette.

The dish was then placed on the vacuum chuck and spun at a rate of 4,000 rpm for 40 seconds to remove excess solution. Rapid changes in the color of the silica film were observed during the first 2–5 seconds of spinning, as the film became thinner.

After spinning, the dishes were placed upright (open part up) on a metal rack. After 40–100 dishes had been spin coated, the rack and dishes were placed in a 50°–70° C. forced air oven for 60 minutes to dry. This drying step is critical to the success of the colloidal silica films of the invention since films which were not given a period of time to dry were easily removed by washing. Drying at an elevated temperature, however, is not required since films dried at room temperature also were found to withstand washing.

4. Washing

After drying, the coated dishes were washed in 1% (vol/vol) sulfuric acid to leach sodium ion and remove unbound colloidal silica. The acid washing is also believed to have removed (deactivated) the biocide included in the LUDOX dispersion by the manufacturer to prevent bacterial and fungal growth during shipping and storage.

Up to 100 dishes were soaked without agitation in 2 liters of acid in a 2 liter Nalgene beaker at room temperature for 30–60 minutes. Dishes were removed from acid, rinsed three times in deionized water and flushed for 30 minutes with 10 liters of flowing deionized water. Dishes were then placed upright in a 50°–70° C. forced air oven for 60 minutes to dry.

5. Sterilization

The dried dishes were placed in foil packages or plastic sleeves and sterilized by gamma irradiation (1.0–2.5 MRad or 10–25 KGrey). The sterile dishes, specifically, those made with the 10× dilution of LUDOX HS-40, were used in the cell culture experiments described below in Example 3.

EXAMPLE 2

Physical and Chemical Characterization Of Colloidal Silica Films

I. Materials and Methods

A. Film Thickness

The thicknesses of spin-coated silica films on polystyrene were measured interferometrically. As a check, films were also formed on polished silicon wafers and their thicknesses were measured using an ellipsometer. The thicknesses measured by the two techniques were in agreement.

B. Film Chemistry

Surface chemistry was studied indirectly by the reaction of the colloidal silica films of the invention with dyes.

Crystal violet lactone (CVL) is a dye which is specific for silanol surfaces. See Iler, R. K., *The Chemistry of Silica,* John Wiley & Sons Inc., NY, 1979, and Turner, U.S. Pat. No. 3,032,401 entitled "Process for Determining Amount and Uniformity of Distribution of Colloidal Silica." As described in the Turner patent, lactone dyes of this kind can be used to determine the amount and uniformity of sprayed colloidal silica on paper by simply comparing the color of the dyed paper with the color of standardized preparations.

A 2% (wt/vol) solution of CVL (Aldrich Chem., Milwaukee, Wis., Catalog No. 332488) in xylene (or $CCl_4$) was used to determine the presence of silanol groups on silica coated polystyrene dishes prepared as described in Example 1. A small amount of the CVL solution (0.2–0.5 ml) was pipetted onto a test dish, swirled, and pipetted off. Slightly yellow when in solution, the CVL dye turns blue when it contacts silanol-containing silica.

Figure 1:
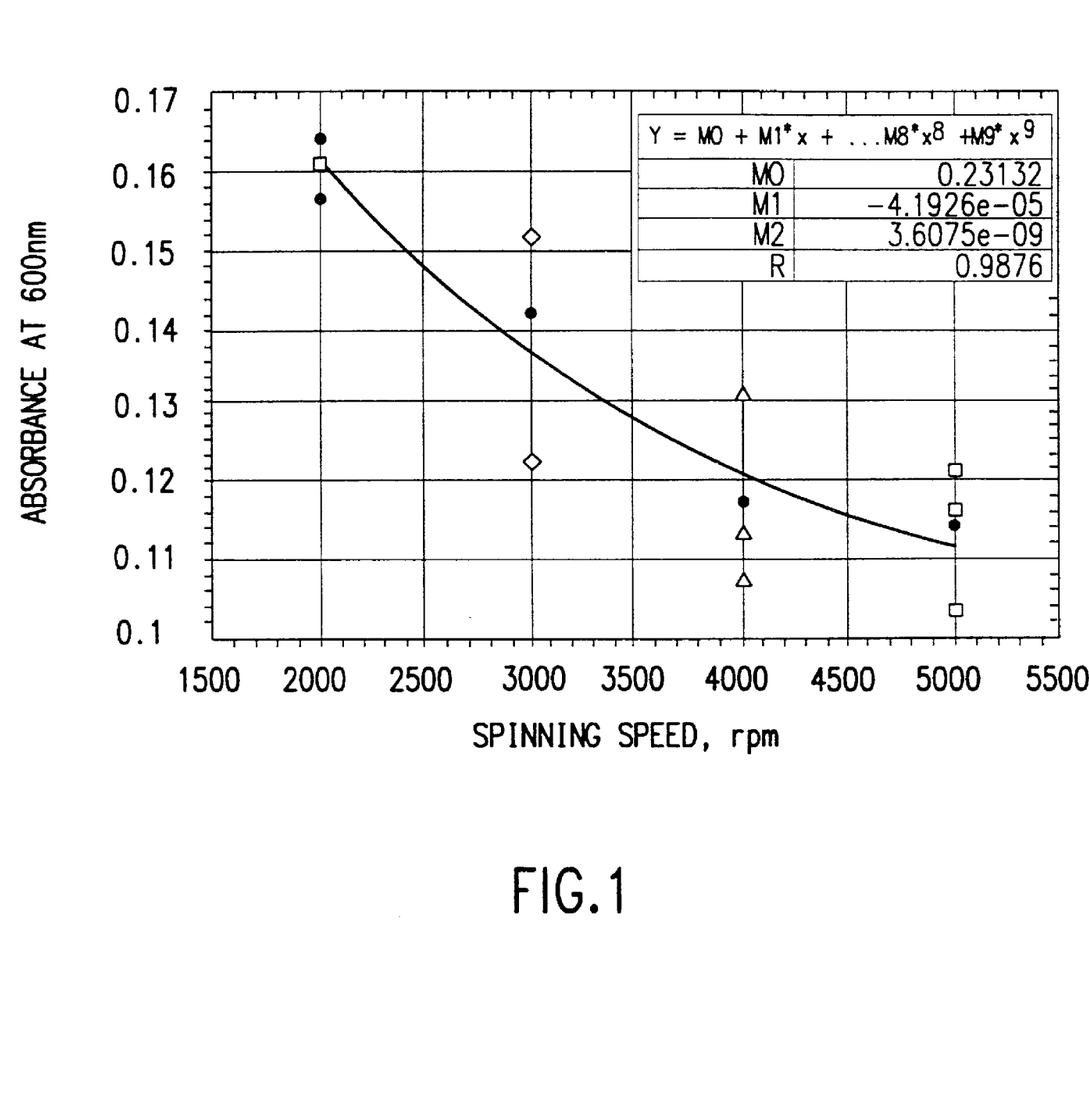
FIG. 1 is a plot of absorbance versus spin speed for dishes coated with a colloidal LUDOX dispersion and dyed with crystal violet lactone (CVL).

The intensity of blue color was quantitated by measuring light absorbance at 600 nm directly through the test dishes using a spectrophotometer. FIG. 1 shows absorbance data for dishes spin coated with a 10× dilution of LUDOX HS-40 at speeds ranging from 2000–5000 rpm. As shown in this figure, dishes coated at a slower speed had higher absorbance values (i.e. thicker films) than those coated at a higher rpm. Films made with the 2× dilution of HS-40 were significantly darker blue than those coated with a 10× dilution.

Crystal violet, an aqueous cationic dye, is commonly used in cell culture. As reported by Rappaport et al. and Carrol & Freeman, this dye is reactive with silica. See Rappaport, C., J. P. Poole and H. P. Rappaport, "Studies on Properties of Surfaces for Growth of Mammalian Cells in Synthetic Medium", *Experimental Cell Research,* Vol. 20, p465–510, 1960; and Carroll, B. and E. Freeman, "The Behavior of Colloidal Silicate Solutions as Revealed by Adsorption Indicators", *J. Phys Chem.,* Vol. 58, p335–338, 1954.

In particular, Rappaport et al. correlated crystal violet dye adsorption with bioactivity of corroded glass surfaces. In their experiments, glass tubes or bottles were soaked in crystal violet for 5 minutes and rinsed with water. Dye was then desorbed with ethanol and solutions were read at 600 nm with a spectrophotometer. Rappaport et al. suggested that glass surfaces which adsorbed more dye had both higher surface area and negative charge. Surfaces with strong crystal violet reactivity performed best in their primary cell cultures.

Rappaport et al.'s crystal violet technique was used as described below to quantitate durability of the colloidal silica films of the invention before and after soaking with various solvents.

C. Microscopy

Optical microscopy of films both dyed and undyed up to 600× were used to determine if the films had microcracks. Scanning electron microscopy (SEM) was performed on surfaces of dishes to determine microtexture of dried films, both as coated and after soaking in buffer.

II. Results

A. Microcracks and Peeling

Films made with 2× dilutions of LUDOX HS-40 (20% $SiO_2$) had microcracks after spin coating while a 2× dilution of LUDOX SK (12.5% $SiO_2$) and a 10× dilution of HS-40 (4% $SiO_2$) did not. The spin speed used for these tests was 4,000 rpm.

The observed microcracks are believed to be due to stresses created during gelation (dehydration) and have the appearance of mudcracks. The microcracks are undesirable since they can lead to peeling of colloidal silica films from their underlying substrates.

The critical parameter is the thinness of the film prior to drying. Accordingly, coating solutions containing higher silica concentrations can be used if the speed of spinning is increased.

The dishes used in the cell culture experiments of Example 3 were coated using the 10× dilutions of LUDOX HS-40 and did not have microcracks.

B. Silanol and Film Coverage

Films made at all of the $SiO_2$ concentrations (i.e., 20%, 12.5%, and 4%) provided an easily observable and essentially homogenous blue reaction with the CVL dye. The films made with more concentrated solutions had a darker reaction indicating more silanol with more silica.

The xylene solvent used in the CVL experiments was found to chemically attack the polystyrene under the colloidal silica film. Specifically, a roughened PS surface was observed. The ability of the solvent to reach the underlying substrate shows that the films were porous.

C. Surface Texture and Chemistry

Porosity and surface texture of dried and carbon-coated colloidal silica films made with LUDOX HS-40 (10× dilution) were investigated by SEM. At magnifications of 5,000–20,000 faint criss-crossing lines were seen. At 100,000×, the only feature that could be seen was a very fine texture in the <10 nm range, with no discernible pores.

Several coated dishes were soaked for 6 days at 37° C. in simulated body fluid (SBF), i.e., a buffered solution having the ionic components and concentration of blood plasma. See Li, P., K. Nakanishi, T. Kokubo and K. deGroot, "Induction and Morphology of Hydroxyapatite, Precipitated from Metastable Simulated Body Fluids on Sol-Gel Prepared Silica", *Biomaterials,* Vol.14, No.13, pages 963–968, 1993. The dishes were then water washed and dried, and assayed for the presence of a calcium-phosphate coating, as is characteristic of bioactive glass. Such a coating was not found. Under the conditions used, NaCl crystals were found. SEMs at 10,000× showed that the treated films had a much coarser surface texture in comparison with films which had not been treated. Chemical analysis by EDAX showed that the film was apparently not chemically modified by adsorption of salts from solution. The film, however, had been physically changed due to hydration and dehydration.

D. Film Thickness

Films formed using a 10× dilution of LUDOX HS-40, a spin speed of 4,000 rpm, and a spin time of 40 seconds, had a thickness of about 50 nm. At the same spinning speed and time, a 2× dilution of LUDOX SK produced a film which was 200 nm thick.

E. Film Distribution and Durability

Crystal violet staining showed that the colloidal silica films formed with LUDOX HS-40 (10× dilution) were homogenous and present on the sides of the dishes as well as the dish bottoms. The presence of the film on the sides of the dishes shows that the coating solution traveled up the side walls during spinning. Some thickening of the film may occur in the corner region where the bottom and side wall meet.

Figure 2:
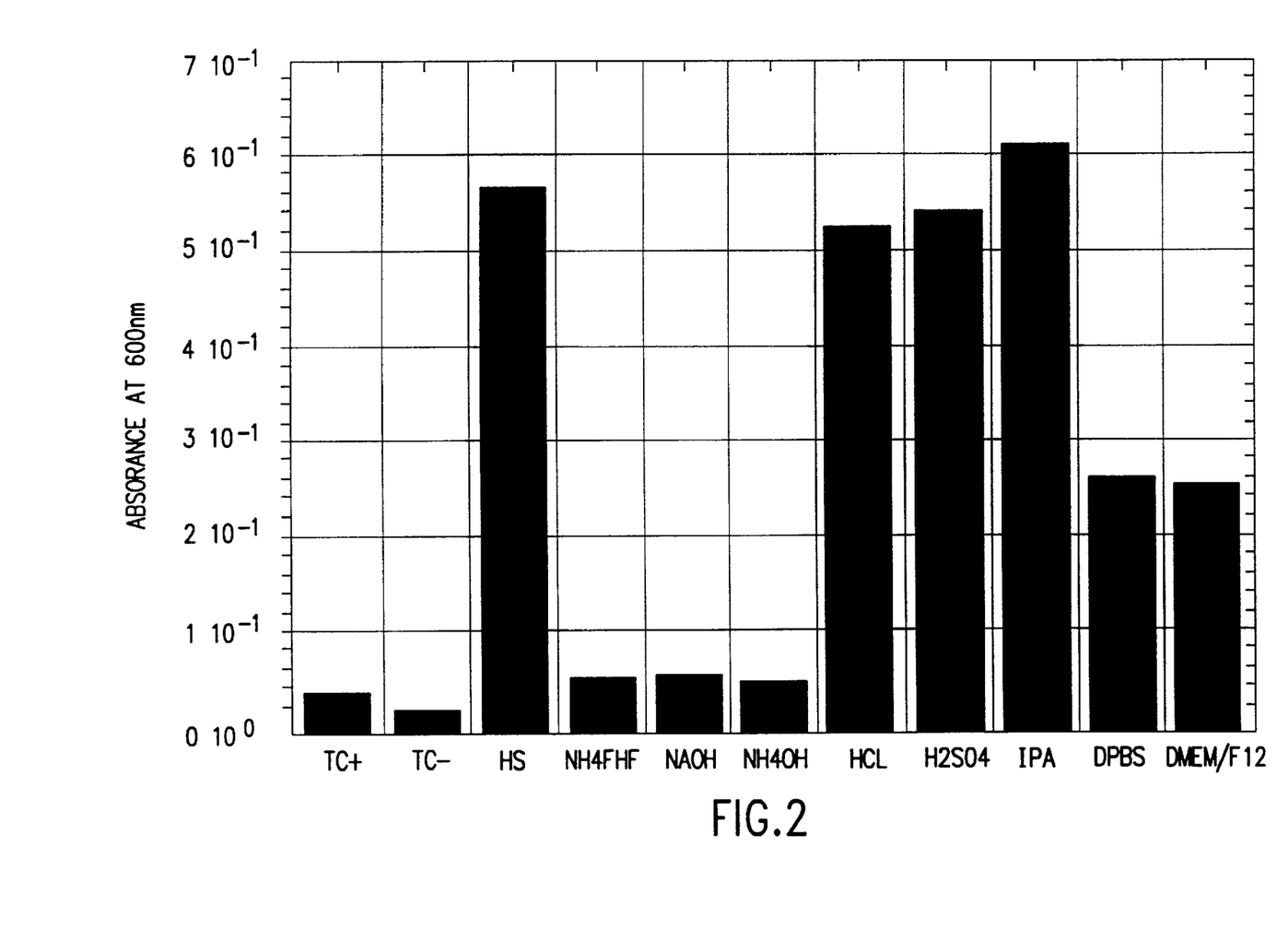
FIG. 2 is a plot showing desorption of crystal violet from dishes coated with a colloidal silica film prepared in accordance with the invention after soaking of the film in various solvents.

FIG. 2 is a graph of absorbance at 600 nm of desorbed crystal violet dye for dishes soaked with various solvents overnight. Uncoated PS, both corona treated (TC+) and untreated (TC−), have very low absorbance values. Dishes (HS) coated with the colloidal silica films of the invention (specifically, dishes coated with LUDOX HS-40 at a 10× dilution) with no solvent soak had values 5–6 times the negative control.

As would be expected, coated dishes soaked with strong alkali or ammonium bifluoride resulted in absorbance levels equal to the uncoated dishes (i.e., the films were removed by dissolution). Dishes soaked with 1M solutions of HCl, $H_2SO_4$, and neat isopropyl alcohol (IPA) resulted in absorbance values near the untreated dishes. Although not tested, the solubility of the films may be much higher in alcohols with a lower MW than isopropyl alcohol. See Iler, R. K., *The Chemistry of Silica,* John Wiley & Sons Inc., NY, 1979.

Dishes soaked with biological buffers (DPBS; DMEM/F12) resulted in values between the negative and positive controls, indicating loss of either negative surface charge and/or surface area after soaking.

F. Dissolution Rate

The dissolution kinetics of the colloidal silica films of the invention was studied by measuring soluble silica levels in buffered solutions which had been in contact with dishes coated with LUDOX HS-40 (10× dilution) at 37° C. for various periods of time.

A DMEM/F12 medium made from powder (Life Technologies, Grand Island, N.Y., Catalog No. 12400) and a DPBS medium were used for these studies. Two milliliters of buffer were added to 35 milliliter petri dishes coated as described above. Solutions from three dishes for each experiment were pooled and assayed. The results obtained are as follows:

| Solution | Exposure Time Hours | [SiO2] ppm |
|---|---|---|
| DMEM/F12 | 0 | <1 |
| DMEM/F12 | 24 | 96 |
| DMEM/F12 | 120 | 154 |
| DPBS | 0 | <1 |
| DPBS | 4 | 6 |
| DPBS | 24 | 24 |
| DPBS | 120 | 107 |

These data show an increase in the level of silica in solution without reaching a plateau level during a five day incubation, i.e., a "slow release" of silica into the medium. More silica was released in DMEM/F12 at pH 8.1 than DPBS at pH 7.2. Increased alkalinity might also explain the relatively high, 154 ppm silica level observed with the DMEM/F12 medium. Note, however, that solutions can peak at a supersaturation level and then reduce to an equilibrium level. See Iler, R. K., *The Chemistry of Silica,* John Wiley & Sons Inc., NY, 1979.

For comparison, $SiO_2$ levels were determined for some other solutions stored in glass bottles. A DMEM/F12 solution (CELLGROW, Mediatech, St. Louis, Mo., Catalog No. 15-090-LV) which is premixed and stored in glass had <1 ppm $SiO_2$. Used and new glass tissue culture Blake bottles were incubated with 25 ml of DPBS solution at 37° C. for five days. These bottles are greenish in color and appear to be made of soda lime glass. No measurable dissolution of silica was detected after 5 days from either the new or used bottles. These results show that the colloidal silica films of the invention are considerably more soluble than used (corroded) glass, due to higher surface area.

The solubility of silica is complex and depends on many factors involving both the silica and the solvent. Dissolution of silica in aqueous media occurs by a hydration reaction, as follows:

$SiO_2 + 2\ H_2O \quad \longleftrightarrow \quad Si(OH)_4$
(silica) (silicic acid)

Silicic acid is very reactive and may combine with inorganic salts or organic compounds in solution or may adsorb back onto silica surfaces. If allowed to dehydrate, silicic acid will polymerize.

As discussed in Iler, the rate of the above reaction depends on various parameters including: silica surface area; surface hydration [Si—OH]; amorphous VS. crystalline silica; silica purity; solvent pH, temperature, and volume; and solvent chemistry (e.g. salt concentration). See Iler, R. K., *The Chemistry of Silica,* John Wiley & Sons Inc., NY, 1979.

G. Property Summary

Table 1 summarizes the properties of the colloidal silica films prepared using the HS-40 and SK dispersions. As shown therein, the colloidal silica films of the invention had a high silanol content and good adhesion to PS. Colloidal silica films have other desirable characteristics including low cost, ease of use, homogeneity, high surface area and wettability. Also, such dispersions are available with a variety of different surface chemistries and particle sizes besides those listed in Table 1.

EXAMPLE 3

Cell Culture on Colloidal Silica Films

I. Materials and Methods

A. General

Two well characterized cell culture systems were used to evaluate the colloidal silica films of the invention, namely, an epithelial cell line (MDCK), and a primary kidney epithelial (proximal tubule explant) preparation. See Taub, M., et al, "Growth of Madin-Darby Canine Kidney Epithelial Cell (MDCK) Line in Hormone-Supplemented, Serum-Free Medium", *Proc. Natl. Acad. Sci.,* Vol. 76, No. 7, pages 3338–3342, 1979; and Jung, J. C., S. Lee, N. Kadakia and M. Taub, "Growth of Primary Rabbit Proximal Tubule Cells in Glucose-Free Serum-Free Medium", *J. of Cell. Phys.,* Vol. 150 pages 243–250, 1992.

For MDCK cells, data was obtained in both serum supplemented and serum-free hormone-supplemented medium; for primary cells, only data for serum-free culture was obtained. Generally, experiments were performed in triplicate. Because specific responses of cells to a new surface is difficult to predict, the cell culture was designed to measure several cell responses, including cell attachment, spreading, growth rate, differentiation, and passageability.

Expression of differentiated function was measured by activity of the brush border enzyme alkaline phosphatase. Passageability was defined as the success in subculturing by trypsinization. Cell morphology by phase contrast microscopy as well as SEM and TEM characterization was determined.

In the results presented below, dishes prepared in accordance with the present invention are referred to as "HS dishes" ("HS surfaces"). The control dishes were conventional, sterile, corona-treated, polystyrene tissue culture dishes referred to as "PS dishes" ("PS surfaces").

B. MDCK Cells With Serum

MDCK cells were plated at $5\times10^3$ cells/dish into 35 mm dishes containing DMEM/F12 medium supplemented with 10% FCS. The cells were incubated at 37° C. in a 5% $CO_2$/95% air humidified environment for 4 days. The cells were then removed from the dishes by means of EDTA trypsin, and counted in a Coulter Counter. Values reported below are the average (±Std. Deviation) of triplicate determinations.

C. MDCK Cells Without Serum

MDCK cells were plated into 35 mm culture dishes containing serum free DMEM/F12 medium supplemented with 5 $\mu$g/ml insulin, 5 $\mu$g/ml transferrin, $5\times10^{-8}$M hydrocortisone, $5\times10^{-12}$M $T_3$ and 25 ng/ml $PGE_1$ at $10^4$ cells per dish. Cells were counted in duplicate dishes in each condition on a daily basis. The growth rate was determined from a plot of $\log_2$ cell number vs. days in culture.

D. MDCK Subcultures

MDCK cells were grown to confluence in serum free Medium K-1. Serum free Medium K-1 contained DMEM/F12 medium supplemented with 5 supplements (5 $\mu$g/ml insulin, 5 $\mu$g/ml transferrin, $5\times10^{-12}$M $T_3$, $5\times10^{-8}$M hydrocortisone, 25 ng/ml $PGE_1$). Subsequently, the cells were plated at $10^4$ cells/dish into 35 mm dishes with either serum free Medium K-1, or DMEM/F12 supplemented with 10% fetal calf serum. The cells were counted after 3 days in a 5% $CO_2$/95% air environment at 37° C. Values reported below are averages (±Std. Deviation) of triplicate determinations.

Growth to confluence was obtained on the HS and PS surfaces in serum free Medium K-1, provided the medium was changed the day after plating and routinely thereafter. After the cells achieved confluence, the cells were subcultured (at $10^4$ cells/35 mm dish) into culture dishes containing either Medium K-1 or DMEM/F12 supplemented with 10% fetal calf serum. The results of this study indicated that following subculturing, the cells could proliferate on both surfaces, both in serum free Medium K-1 and in DMEM/F12 medium supplemented with 10% fetal calf serum. Although not wishing to be bound by any particular theory of operation, the growth obtained with the HS substratum in serum free Medium K-1 could be attributed to the routine medium changes conducted in this experiment.

E. Serum Free Primary Kidney Cultures

Primary cultures of rabbit kidney proximal tubule cells were grown in serum free DMEM/F12 supplemented with 5 $\mu$g/ml insulin, 5 $\mu$g/ml transferrin, and $5\times10^{-8}$M hydrocortisone. The cultures were maintained in a 37° C., 5% $CO_2$/95% air humidified environment for 20 days with routine medium changes. The number of cells in the culture dishes was then determined utilizing a Coulter Counter. Values reported below are averages (±Std. Deviation) of triplicate determinations.

Experiments were performed with the tubular material plated into the dishes at a density leading to high growth rates on polystyrene and at a considerably lower density (⅙ of the normal plating density). Growth was obtained on both the HS and PS surfaces at both densities.

Growth in the above serum-free medium occurred without fibroblast overgrowth. Growth on HS and PS surfaces was also observed in a glucose free medium, indicative of gluconeogenic capacity, typical of the renal proximal tubule.

F. Alkaline Phosphatase Activity of Primary Cultures

Primary rabbit kidney proximal tubule cells exhibit a polarized morphology in vitro as observed in the in vivo situation. The cells retain an apical surface with microvilli (i.e. a brush border), and brush border enzymes. The level of a particular brush border enzyme, alkaline phosphatase, was examined in primary cultures maintained on HS and PS surfaces.

Specifically, primary cultures were grown to confluence in serum-free DMEM/F12 medium supplemented with 5 $\mu$g/ml insulin, 5 $\mu$g/ml transferrin, and $5\times10^{-8}$M hydrocortisone. The cultures were then utilized for alkaline phosphatase assays as described by Taub, M., Laurie, G. W., Martin, G. R., and Kleinman, H. K., "Altered Basement Membrane Protein Biosynthesis by Primary Cultures of CPK/CPK Mouse Kidney," *Kidney International,* Vol. 37, 1990, pages 1090–1097. Alkaline phosphatase activity was determined by the rate of release of p-nitrophenol from p-nitrophenolphosphated. Values are the average of triplicate determination.

G. Primary Kidney Subcultures Without Serum

Cells were passaged from a particular substratum (e.g. HS) to the same substratum (e.g. HS). When passaging at a 1:3 passage ratio, the first passage cells on HS and PS appeared to grow similarly initially. After two weeks, first passage cells on HS were observed to form confluent monolayers which formed many huge, multicellular domes, indicative of the capacity for transepithelial solute transport. Previously, domes have not typically been observed in first passage cultures, although their appearance has been observed in confluent monolayers of primary cultures on normal plastic.

The rabbit kidney proximal tubule cells were also passaged at a low passage ratio (1:20). The cells also survived at this passage ratio. Cells on PS began to senesce (as indicated by a very enlarged morphology), whereas cells on HS retained a normal epithelial morphology.

H. Attachment of Rabbit Kidney Proximal Tubules

Primary rabbit kidney proximal tubule cells were initiated by plating purified nephron segments onto HS and PS dishes. The next day the number of tubules attached in 20 microscope fields was determined at 100× magnification under an inverted microscope. The number of tubules attached per microscope field is the average from determinations made in three dishes, for each condition.

II. Results

A. MDCK Cells With Serum

Figure 3A:
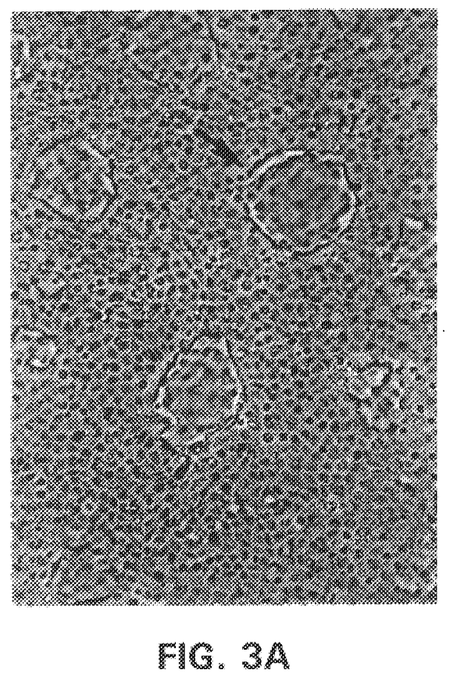
FIGS. 3A, 3B, and 3C are photomicrographs of MDCK cells grown on a polystyrene surface (FIG. 3A) and a polystyrene surface coated with a colloidal silica film prepared in accordance with the invention (FIGS. 3B and 3C). The growth medium for these figures included serum.
Figure 3B:
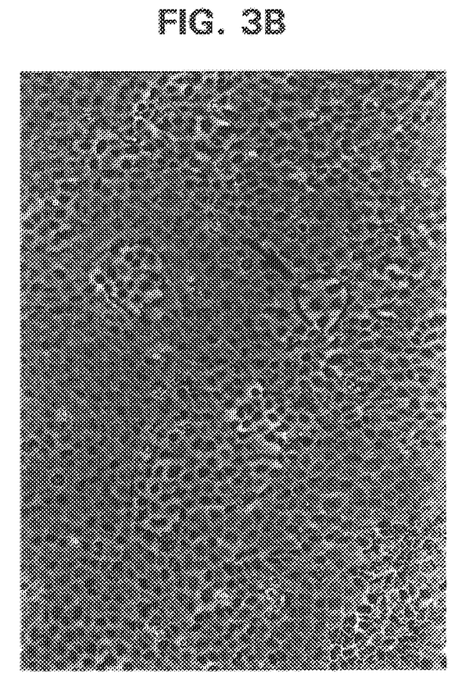
Figure 3C:
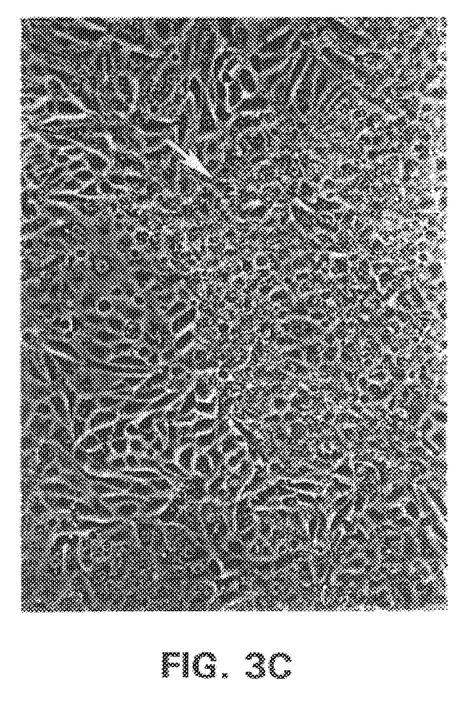

MDCK cells with serum attached, spread and reproduced on both HS and PS dishes. Average cell number per HS dishes was 70% of the cell number in the PS control dishes after four days (53,860±3,400 for HS versus 77,060±11,200 for PS). Cell morphology by phase contrast was cuboidal or cobblestone-like and similar for cells in HS and control dishes. See FIG. 3. MDCK monolayers on HS dishes exhibited more growth after confluency than PS cells (white arrow), and were apparently more metabolically active than on PS, as the medium was relatively more acidic.

A phenomenon called "doming", or hemispherical blistering, which is indicative of actively transporting cell monolayers was found in both control PS and HS dishes. Domes are multicellular areas of a cell monolayer which are slightly elevated from the dish and appear as raised round areas on PS and HS dishes as in FIG. 3 (black arrow).

In order for doming to occur three cell conditions are required: functional plasma membrane polarization, formation of occluding junctions (e.g. tight junctions), and vectoral transepithelial active ion transport. See Lever, J. E., "Inducers of Dome Formation in Epithelial Cell Cultures Including Agents That Cause Differentiation", Chap. 1 in *Tissue Culture of Epithelial Cells,* Ed. M. Taub, Plenum Press, NY, 1985. Doming does not occur on porous supports such as collagen-coated mesh or nitrocellulose filters since fluid accumulation on the basolateral side is prevented. See Cereijido, M., et al, "Polarized Monolayers Formed by Epithelial Cells on Permeable and Translucent Support", *J. of Cell Biology,* Vol. 77, pages 853–880, 1978. Apparently, the HS surface is as inductive to the cell conditions required for doming as PS, and does not provide enough porosity when wet to allow "leaking" which would preclude dome formation.

B. MDCK Cells Without Serum

MDCK cells without serum responded very differently in HS dishes than in PS dishes. On HS, the cells appeared epithelial in morphology; on PS, the cells appeared to be epithelial, but more spread out than on HS.

Figure 4A:
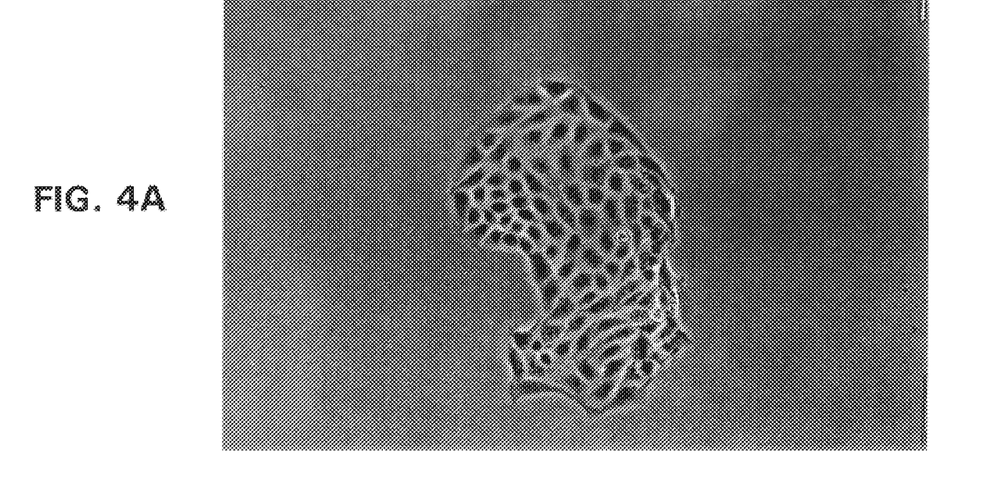
FIGS. 4A and 4B are photomicrographs of MDCK cells grown on a polystyrene surface (FIG. 4A) and a polystyrene surface coated with a colloidal silica film prepared in accordance with the invention (FIG. 4B). The growth medium for these figures was serum free.
Figure 4B:
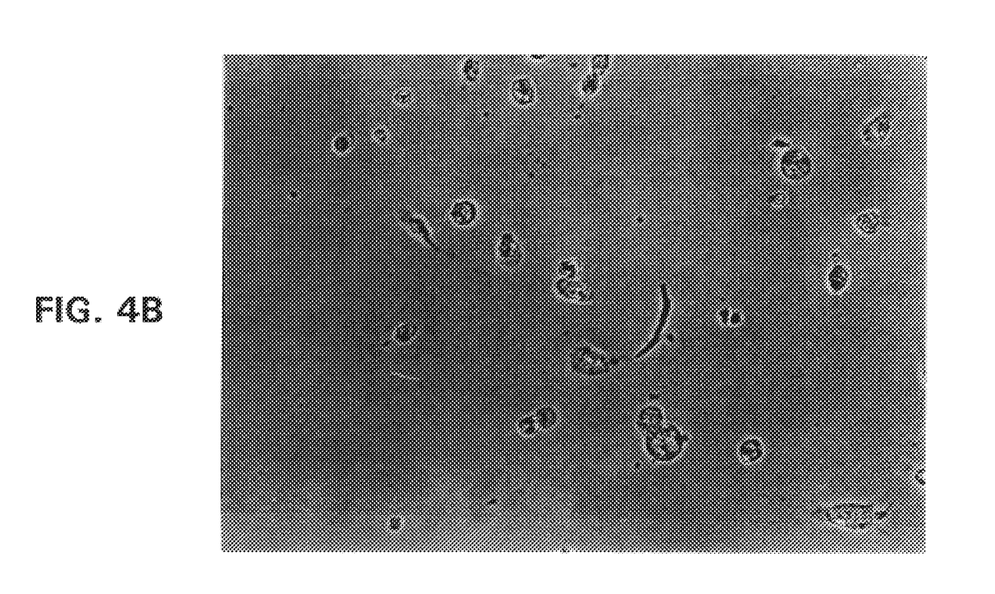

Cells on PS attached, spread and grew (perhaps via cell membrane bound ligands, since cultures were serum-free). Cells on HS dishes attached but did not spread or grow. See FIG. 4. The growth rate on HS was insignificant, 0.06 doublings/day compared to 1.8 for the PS control dishes. Confluence was achieved within the 7 day culture period for the PS dishes; confluence was not achieved for the HS dishes within this period.

Lack of mitosis in cells which have not spread is not surprising in light of what is known concerning cell spreading and proliferation in culture. The frequency of cell division has been observed to increase with experimentally controlled increases in cell spreading. A current theory is that a more well-spread cell can capture more growth factors and take up larger quantities of nutrients due to its larger surface area. See Alberts, B., et al, *Molecular Biology of the Cell,* 3rd Ed., Garland Publishing Inc., NY, page 969, 1994.

Since cells attached and spread on PS, lack of an adhesion-promoting ligand will not explain why the cells did not spread on the HS surface. Although not wishing to be bound by any particular theory of operation, it is possible that there may be a difference in the adhesion of an attachment-promoting ligand to the colloidal silica substrate vs. the polystyrene substrate, which did not allow the development of focal contacts and cell spreading. Other hydrated "gels" inhibit extensive cell spreading as well (e.g., MATRIGEL manufactured by Collaborative Biomedical Products, Bedford, Mass.).

When daily medium changes were initiated by 24 hours after plating, MDCK cells spread and reproduced to confluency in serum-free culture on HS dishes. This result suggests that either the removal of an attachment inhibiting factor or the addition of fresh attachment factors was necessary for serum-free MDCK spreading on HS. The latter possibility, however, seems unlikely since the medium is serum-free.

Chemical analysis of spent medium from several pooled MDCK HS dishes revealed that about 100 ppm of $SiO_2$ had become dissolved into the medium from the HS surface (probably as $Si(OH)_4$). Although again not wishing to be bound by any particular theory of operation, it is possible that soluble silica may have acted as a spreading inhibitor. Serum-free cell cultures are typically more sensitive to inhibitory factors than are serum-containing cultures, perhaps because serum components inactivate inhibitory factors in medium. In the case of MDCK cultures with serum on HS dishes, serum components may adsorb onto the colloidal silica and reduce or eliminate subsequent silica dissolution, minimizing soluble silica effect.

C. MDCK Subcultures

MDCK cells grown to confluence on HS and PS in serum-containing media could be readily subcultured onto the same type of surface. Subculturing was successful not only when the cells were split at a high ratio (e.g., 1:2), but also at much lower subculturing ratios (1:10, 1:20, 1:50). The cells grew to confluence. As discussed above, confluent MDCK monolayers on HS dishes exhibited considerable cell growth and appeared to be more metabolically active than cells on PS dishes, as the medium was relatively more acidic.

MDCK cells were grown to confluency without serum on HS and PS dishes, then released with enzyme, washed and plated into new dishes of the same type, both with and without serum. The serum-free PS dishes plated onto serum-free PS dishes were used as the positive control at 100% cell number.

On PS dishes, serum and serum-free subcultures grew at equivalent rates of 106%±3% and 100%±13% after 3 days. HS subcultures which were provided with serum grew to 118%±33%) of the control cell number, indicating inhibition of cell spreading and growth was not a "transferred" state after exposure to HS surfaces serum-free. Serum-free HS subcultures remained spreading and growth inhibited at 3%±0% of the control cell number. Although again not wishing to be bound by any particular theory of operation, these experiments indicate that an extracellular effect rather than an intracellular effect is likely the cause of spreading inhibition seen for the serum-free HS cultures.

D. Serum Free Primary Kidney Cultures

Several differential advantages were identified for cultures of primary explants on HS vs. PS. As is often the case with primary cells and cell lines which have been adapted to growth on PS surfaces, kidney primaries behaved differently than the MDCK cell line.

First, attachment of kidney tubule explants (nephron segments) was better on HS than PS. This was most apparent in an experiment in which the tissue preparation was suboptimal in that poor attachment to the PS control surface was observed. Under these conditions, 10 times more tubule segments attached per microscope field on HS dishes compared to PS dishes (16±5 tubule segments/microscope field for HS versus 1.6±1.4 tubule segments/microscope field for PS). Under conditions more conducive to attachment, the HS dishes continued to achieve higher attachment levels than the PS dishes (10.7±1.0 tubule segments/microscope field for HS versus 4.6±1.0 tubule segments/microscope field for PS).

The mechanism for attachment of tissue is not as well defined as the attachment of individual cells (i.e. integrin receptors and ligands are not as well defined). Although again not wishing to be bound by any particular theory of operation, in the case of HS dishes, the attachment may be due to an affinity of negatively charged silica gel for collagen.

Figure 5A:
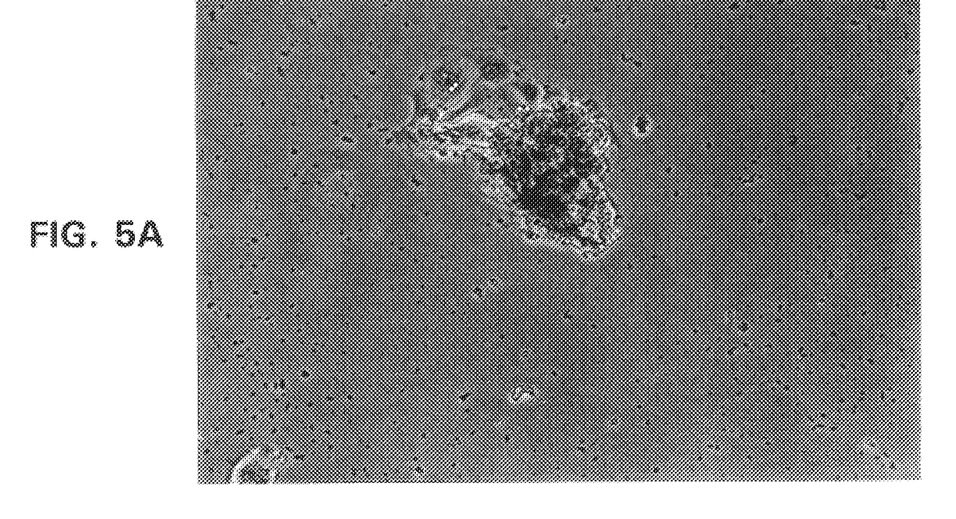
FIGS. 5A and 5B are photomicrographs of cells growing from primary rabbit kidney proximal tubule explants on a polystyrene surface (FIG. 5A) and a polystyrene surface coated with a colloidal silica film prepared in accordance with the invention (FIG. 5B).
Figure 5B:
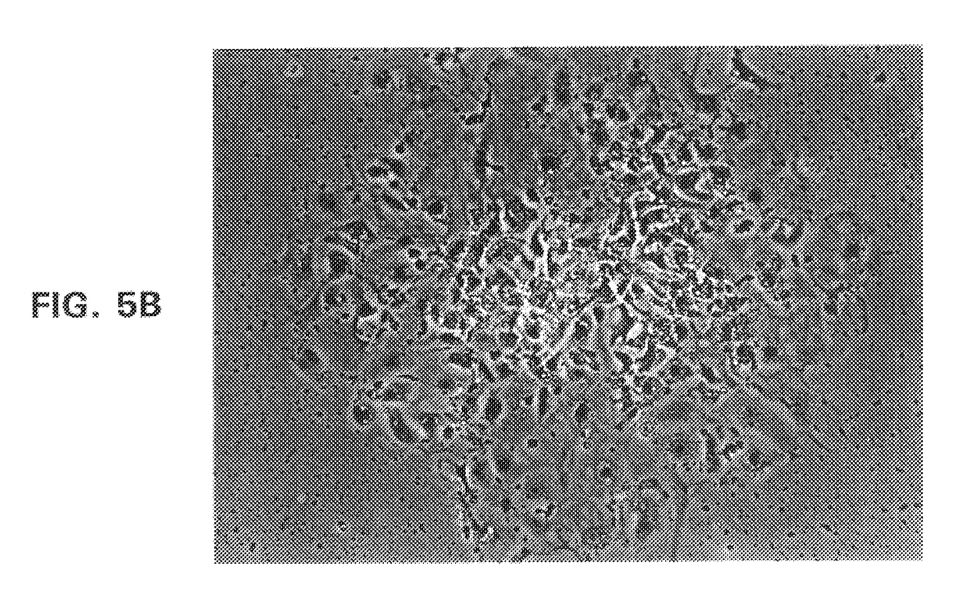

FIG. 5 shows outgrowth of cells from explants in culture. Cells at this stage on HS dishes had significantly more intracellular vesicles than cells on PS dishes. The vesicles are white by phase contrast microscopy and their significance is not known.

Second, kidney cells reproduce from explants faster on HS dishes than on PS. One culture set had an average number of cells/dish on HS at day 10 of nearly 3.5 times that of PS. Cells were counted at day 20 in another experiment and approximately 1.6 times more cells were found on the HS dishes in comparison to the PS dishes (83,360±14,311 cells/dish for HS versus 51,563±17,715 cells/dish for PS).

Confluent primary cultures on HS dishes demonstrated approximately 2.8 times more alkaline phosphatase activity than equivalent PS cultures (22.6±5.4 nmoles p-nitrophenol/mg protein/minute for HS versus 8.2±1.7 nmoles p-nitrophenol/mg protein/minute for PS). In subsequent experiments, this difference was found to be variable but in all cases the HS surface was found to be as good as or better than the PS surface in terms of alkaline phosphatase activity.

The third, and perhaps most significant advantage of colloidal silica films in primary cultures was seen upon subculturing. Cells were removed from surfaces with enzyme treatment as easily from HS as PS dishes and were subcultured on like substrates. The cells retained an epithelial morphology, particularly when grown on the HS surface.

The subcultured cells on HS dishes recovered from trypsinization more slowly than the control dishes, but cells eventually grew to confluency and maintained a more differentiated morphology. Populations of cells in subcultures on PS typically become senescent to a greater degree, with larger individual cells and a lack of doming upon confluency. Cells subcultured on HS dishes retained cuboidal morphology and formed large domes.

Although not wishing to be bound by any particular theory of operation, primary cultures may have been more successful on the colloidal silica films than the MDCK cells (without serum) because the primary cells bring along more extracellular matrix (ECM) components and apparently have a "window of opportunity" to make some ECM after attachment of explant tissue, to "condition" the substrate for adhesion and spreading.

Further, a competition for cell adhesion promoting ligands may exist between soluble silica and cells in culture. This could explain why frequent removal of soluble silica promotes spreading in serum-free MDCK cultures. Primary kidney cells may produce an amount of ligand great enough to overcome the loss due to soluble silica.

Although not wishing to be bound by any particular theory of operation, it is believed that insight into the foregoing cell culture results can be obtained from considerations of the in vivo behavior of silicon-containing materials. In particular, evidence of a "natural" affinity for silica gel and ECM components can be found in the literature.

The mechanism for the tissue bonding phenomenon found in silicate implants has been explored by Larry Hench and others. See Hench, L. L. and J. Wilson, "Bioceramics", *MRS Bull.*, Vol. 16, No. 9, 1991, pages 62–74; Hench, U.S. Pat. No. 4,171,544 entitled "Bonding of Bone to Materials Presenting a High Specific Area, Porous, Silica-Rich Surface"; Ohura, K., et al, "Bone-bonding Ability of P2O5-Free CaO-SiO2 Glasses", *J. of Biomed. Mats. Res.*, Vol. 25, 1991, pages 357–365; and Li, P. et al, "Process of Formation of Bone-like Apatite Layer on Silica Gel", *J. of Mats. Sci.: Mats. in Med.*, Vol. 4, 1993, pages 127–131.

The key surface component for tissue bonding is reportedly silanol groups at the implant-tissue interface. It has been shown that the silanol surface supports the attachment of ECM components which enable cell attachment and growth in vivo and in vitro. Silanol-rich surfaces are also credited with the nucleation of crystals of hydroxylapatite [$Ca_5(PO_4)_4(OH)$] which become new bone surrounding and firmly attached to bone implants. Hench recognized the importance of "high specific area, porous, silica-rich surfaces" in bone bonding, giving porous VYCOR and Portland cement as examples in his U.S. Pat. No. 4,171,544.

BIOGLASS implants (U.S. Biomaterials, Alachua, Fla.) bond to bone and soft tissue by forming an intermediate silica gel/calcium phosphate/ECM "seam" in vivo. The ability of these glasses to bond to soft and hard tissue is dependent on the corrosion processes that take place within minutes after implantation and these corrosion and mineralization phenomena have been extensively detailed. Collagen as well as glycosaminoglycans (GAG's) has been found to be incorporated into corroding BIOGLASS surfaces in vitro. See Hench, L. L., "Bioceramics", *MRS Bulletin*, Vol. 16, No. 9, pages 62–74, 1991.

Sol-gel derived porous silica substrates have been found bioactive by Tadashi Kokubo at Kyoto University in Japan. Kokubo and others in the biomaterial field have found that the key to "bioactivity" is the rate of hydroxylation and quantity of silanol groups on an implant surface. Ohura, K., et al, "Bone-bonding Ability of P2O5-Free CaO-SiO2 Glasses", *J. of Biomed. Mats. Res.*, Vol. 25, 1991, pages 357–365; Li, P. et al, "Process of Formation of Bone-like Apatite Layer on Silica Gel", *J. of Mats. Sci.: Mats. in Med.*, Vol. 4, 1993, pages 127–131; and Li, P., I. Kangasneimi, K. deGroot, T. Kokubo, and A. U. Yli-Urpo, "Apatite Crystallization from Metastable Calcium Phosphate Solution on Sol-Gel-Prepared Silica", *J. of Non-Crystalline Solids*, Vol. 168, 1994, pages 281–286.

The role of silicon as an essential trace element in the formation of connective tissue was presented by Birchall and Carlisle as determined by animal nutrition studies. See Birchall and Chappel, supra; and Carlisle, E. M., "Silicon as an Essential Trace Element in Animal Nutrition", in *Silicon Biochemistry*, eds. D. Evered and M. O'Connor, John Wiley & Sons Ltd, Sussex, UK, 1986;

A look at the molecular biology of silicon was given by Schwarz's discovery of a bound form of silicon in GAG's and polyuronides purified from human umbilical cord tissue. See Schwartz, K. , "A Bound Form of Silicon in Glycosaminoglycans and Polyuronides", *Proc. Nat. Acad. Sci., USA*, Vol. 70, No. 5, page 1608–1612, 1973. Between 330–554 ppm of Si was found in hyaluronic acid and chondroitin 4-sulfate. The bonding of silicon was thought to be covalent via silanolate (Si—O—C) linkages, and in this way acts as a crosslinking agent in connective tissues. Such a bond may be involved in holding the colloidal silica films of the present invention to corona treated PS dishes.

Barnes et al. reported the use of glass beads in an affinity chromatography column for separation of fibronectin, vitronectin and other adhesion-promoting ligands from human serum. See Barnes, D., et al, "Glass-Bead Affinity Chromatography of Cell Attachment and Spreading-Promoting Factors in Human Serum", *Anal. Biochem.*, Vol. 137, pages 196–204, 1984. Glass beads were prepared by soaking overnight in concentrated acid, washing with distilled water, and equilibrating with sodium carbonate at pH 8. Serum was depleted of adhesion-promoting ligands at pH 8 and ligands were eluted from the columns after changing to pH 9. A sufficiently high ratio of glass bead surface area to serum volume was required. Maintaining an alkaline environment before and during chromatography was required for separation. Barnes et al state that "It is intriguing that serum SF, fibronectin, and laminin all exhibit similar properties regarding binding to and elution from glass beads, suggesting that this property may be related in some way to the biological activities of these three cell attachment and spreading promoting glycoproteins".

Barnes et al. also noted that other serum proteins (e.g. growth factors) may have been depleted by this treatment. They tested for the possibility of the chromatography introducing a cell spreading inhibitor, by adding back ligand to chromatography-depleted serum, and found no inhibitory effect on cells. Barnes et al. did not determine the surface chemistry of their glass, but their procedure suggests a highly reactive, leached, silica gel surface layer was formed. Increasing pH to 9 may have released ligands by dissolution of underlying silica.

Increased metabolic rates for cells grown on glass have been previously reported. Warren et al. reported a three to four times increase in uptake of radio-labeled glucosamine by a kidney cell line (BHK) grown on glass (Blake bottles) compared to plastic flasks. See Warren, L., D. L. Blithe and G. Cossu, "Variation in the Carbohydrates of Glycoproteins of Cells Growing on Different Surfaces", *J. of Cell. Phys.*, Vol. 113, pages 17–22, 1982. Warren et al. also cited a variation in the carbohydrates of glycoproteins (by SDS-PAGE) of cells growing on those substrates.

EXAMPLE 4

Comparative Example

Corona treated PS dishes were coated with a mixture of PAO4 and LUDOX HS-40 colloidal silica (referred to hereinafter as "PA dishes" ("PA surfaces"). PAO4 is a polyacrylamide material made by BSI Corporation (Eden Prairie, Minn.) which is photo-linkable to PS. Dishes were wet coated using a pour-on-pour-off technique and UV irradiated prior to gamma sterilization. These coatings were clear but inhomogeneous. Micron-sized silica particles were found on the surface of the coatings. These particles stained blue with CVL dye, but the overall coating did not, indicating low dispersion of silanol in the coating. SEM micrographs and EDAX analysis supported the CVL observations. A summary of the properties of this coating appears in Table 1.

MDCK and primary cell culture experiments were performed with the PA dishes following the procedures of Example 3. These experiments showed that with regard to MDCK cells, the PA surface was intermediate between the PS and HS surfaces (MDCK cells with serum—53,860±3,400 cells per 35 mm dish for HS versus 77,060±11,200 for PS versus 58,860±4020 for PA; MDCK cells without serum—0.06 doublings/day for HS versus 1.8 for PS versus 1.0 for PA; serum and serum-free subcultures—118%±33% and 3%±0% of control for HS versus 106%±3% and 100%±13% for PS versus 115%±11% and 9%±0% control for PA). With regard to primary cells, the PA surface produced less growth than either the PS or the HS surfaces (83,360±14,311 cells/dish for HS versus 51,563±17,715 for PS versus 31,360±220 for PA).

This data show the importance of having Si—OH groups throughout the film for primary cell growth in serum free media. As discussed above, instead of having uniformly distributed silica, the PA films only had localized silica particles. These particles did not provide sufficient silanol groups to produce the enhanced primary cell growth achieved with the HS films.

Although preferred and other embodiments of the invention have been described herein, further embodiments may be perceived by those skilled in the art without departing from the scope of the invention as defined by the following claims.

TABLE 1

Silicate Coatings for Cell Culture

| Spin Coated Films | Si—OH (CVL dye) | Adhesion to TC PS | Thickness (interferometer) nm | Pores? (xylene) | Appearance | Post-spin treatment | Non-SiO2 Component |
|---|---|---|---|---|---|---|---|
| Ludox (10% HS-40) | yes | yes | 50 | micro | clear | short washes | none |
| Ludox (50% SK) | yes | yes | 200 | micro | clear | short washes | PVA |
| Wet Ctd PAO4 + Ludox HS-40 | no | yes | unmeasured | N/A | clear (Si debris) | N/A | polyacrylamide |

What is claimed is:

1. An apparatus for growing cells in culture comprising a substrate at least a portion of which is coated with a colloidal silica film.

2. The apparatus of claim 1 wherein the substrate has a wettable surface.

3. The apparatus of claim 1 wherein the substrate is composed of a polymeric material.

4. The apparatus of claim 1 wherein the colloidal silica film is porous.

5. The apparatus of claim 1 wherein the colloidal silica film contains reactive Si—OH groups.

6. The apparatus of claim 1 wherein the colloidal silica film is partially soluble in culture medium.

7. The apparatus of claim 1 wherein the colloidal silica film has a thickness of less than about 100 nanometers.

8. The apparatus of claim 1 wherein the colloidal silica film supports to the growth of primary cells in a serum-free medium.

9. The apparatus of claim 1 wherein the colloidal silica film produces enhanced growth of said cells in a serum-free medium in comparison to the growth that would have been produced had said substrate been uncoated under comparable conditions.

10. A method for growing cells comprising applying a culture medium and the cells to be grown to the colloidal silica film of the apparatus of claim 1.

11. The method of claim 10 wherein the cells are primary cells.

12. The method of claim 11 wherein the culture medium is serum free.

13. A method for producing apparatus for performing cell culture comprising:
(a) providing a cell culture substrate;
(b) applying an aqueous dispersion of colloidal silica to at least a portion of the substrate; and
(c) drying at least a portion of the aqueous dispersion on the portion of the substrate to form a film, said film serving as an attachment surface for the growth of cells in culture.

14. The method of claim 13 wherein the substrate has a wettable surface.

15. The method of claim 13 wherein the substrate is composed of a polymeric material.

16. The method of claim 13 wherein the film is porous.

17. The method of claim 13 wherein the film contains reactive Si—OH groups.

18. The method of claim 13 wherein the film is partially soluble in culture medium.

19. The method of claim 13 wherein the film has a thickness of less than about 100 nanometers.

20. The method of claim 13 wherein the film supports to the growth of primary cells in a serum-free medium.

21. The apparatus of claim 20 wherein the colloidal silica film produces enhanced growth of said cells in a serum-free medium in comparison to the growth that would have been produced had said substrate been uncoated, under comparable conditions.

22. The method of claim 13 wherein the concentration of silica in the aqueous dispersion is less than about five weight percent.

* * * * *